US00PP31407P2

(12) United States Plant Patent
Ren et al.

(10) Patent No.: US PP31,407 P2
(45) Date of Patent: Jan. 28, 2020

(54) MUSCADINE GRAPE PLANT NAMED 'FLORIDA ONYX'

(50) Latin Name: ***Vitis rotundifolia* Michx.**
Varietal Denomination: Florida Onyx

(71) Applicant: Florida A&M University, Tallahassee, FL (US)

(72) Inventors: Zhongbo Ren, Tallahassee, FL (US); Jiang Lu, Shanghai (CN); Violeta Tsolova, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 15/999,995

(22) Filed: Sep. 7, 2018

(51) Int. Cl.
*A01H 5/08* (2018.01)
*A01H 6/88* (2018.01)

(52) U.S. Cl.
USPC ..... Plt./206

(58) Field of Classification Search
USPC ..... Plt./205, 206
See application file for complete search history.

(56) References Cited

U.S. PATENT DOCUMENTS

PP4,771 P 9/1981 Fry
PP5,824 P 12/1986 Ison
PP7,267 P 7/1990 Ison

OTHER PUBLICATIONS

UPOV-PLUTO Plant Variety Database—Jun. 4, 2019, cultivar name for 'Onyx' (1 page total).*

* cited by examiner

*Primary Examiner* — Susan McCormick Ewoldt
(74) *Attorney, Agent, or Firm* — Steven M. Forte; Smith & Hopen, P.A.

(57) ABSTRACT

A new and distinct cultivar of the muscadine grape plant, *Vitis rotundifolia* Michx., which is highly productive, resistant to Pierce's disease, low fruit ripening rot, and relatively low wet scar. The new and distinct cultivar has a very large deep black-red colored berry with an extremely pleasant fruit flavor. The cultivar has moderate vine growth with high fruit yield, and very good disease resistance. The cultivar also has an extended shelf life.

2 Drawing Sheets

FEDERALLY SPONSORED RESEARCH OR DEVELOPMENT

This research was supported by the Florida Department of Agriculture and Consumer Services.

Genus and species of new cultivar: *Vitis rotundifolia* Michx.

BACKGROUND OF THE INVENTION

The muscadine grape, *Vitis rotundifolia* Michx., is native fruit grown in the Southeastern United States. In the North Florida climate, it ripens in late August when few other fruits are in season. The berries are large, as compared to other grape species, and are borne in small clusters of 5-10. When fully ripe, the berries on some previously existing cultivars such as 'Dixieland' (U.S. Plant Pat. No. 4,771) are generally bronze, but the berries on other preexisting cultivars can range from red to black with slightly raised lenticels, giving a somewhat mottled appearance.

'Supreme' (U.S. Plant Pat. No. 7,267) is a muscadine grape cultivar introduced in the late 1980s for the fresh fruit market in the Southeastern United States. It was developed from a cross between the female variety 'Black Fry' (U.S. Plant Pat. No. 5,824) and the pollen parent 'Dixieland' made by Mr. W. G. Ison. 'Supreme's' distinguishing features were that it was an improved variety at the time of its release of the muscadine grape, and the large sized black berry. 'Black Fry' was developed from a cross between the female variety 'Fry' (unpatented) and the pollen parent variety 'Cowart' (unpatented), also made by Mr. Ison. 'Black Fry's' distinguishing features were that its characteristics, such as quality, shelf life, and sugar content were superior to both parents.

'Black Beauty' (U.S. Plant Pat. No. 7,592) is a muscadine grape cultivar introduce by Ison nursery in 1991. 'Black Beauty' is the best self-fertile available.

Despite these distinguishing characteristics of 'Supreme', 'Fry', and 'Black Beauty', customers are always looking for a variety with even bigger berries. Furthermore, we have found that the yields for 'Supreme' and 'Fry' were inconsistent in different years and locations; the fruits of 'Black Beauty' are somewhat smaller than the expectations of customers; the size of 'Supreme' fruits were inconsistent. Thus, there has been a need to develop a new cultivar that has a berry size that is larger than the current muscadine variety and has a firm flesh texture with relatively thin skin and good favor, which also retains important agronomic characteristics such as vigorous growth, disease resistance and very low fruit rot. Additionally, there is a need to develop a muscadine grape plant cultivar with a relatively low wet scar, minimal berry damage and improved shelf life for the fresh fruit market.

BRIEF SUMMARY OF THE INVENTION

The present disclosure comprises a new and distinct plant cultivar of *Vitis rotundifolia* Michx., which has been named 'Florida Onyx'. 'Florida Onyx' is a new muscadine cultivar bred for the fresh fruit grape industry in Florida and the Southeastern United States. 'Florida Onyx' is a pistillate (female) grape vine that is highly productive, resistant to Pierce's disease (PD), low fruit ripening rot (ripe rot, and bitter rot), and relatively low wet scar. The most outstanding characteristics of 'Florida Onyx' are very large deep black-red colored berry with extremely pleasant fruit flavor.

The following traits have been repeatedly observed and are the most pronounced characteristics of this new cultivar when grown in Florida, and which in combination distinguish it from existing cultivars:

1) Moderate vine growth with high fruit yield, and very good disease resistance.
2) Very large black-red colored fruit, which is 3-4 grams superior than the largest muscadine varieties on the market.
3) Very good favor.
4) Low fruit rot and relatively low wet scar.
5) Extended shelf life.

BRIEF DESCRIPTION OF THE DRAWINGS

The accompanying color photographs show a representative section of a typical specimen of the new cultivar.

FIG. 1 is a detailed view of several clusters of ripe berries, obtained by clipping away some foliage of a 13-year-old vine.

FIG. 2 is a detailed view of several clusters of ripe berries in comparison to a golf ball to better show the size of the ripe berries of a 13-year-old vine.

DETAILED BOTANICAL DESCRIPTION

In the following description, color references are made as per *The Royal Horticultural Society Colour Chart* (R.H.S.), The Royal Horticultural Society, London, 2015 (sixth edition) except where general terms of ordinary dictionary significance are used.

Origin of the Cultivar

'Florida Onyx' was developed under the grape breeding program of the Center for Viticulture and Small Fruit Research, Florida A&M University (FAMU), Tallahassee, Fla. 'Florida Onyx' originated from a seedling population crossed between *Vitis rolundifolia* Michx. cultivars originated from a seedling population crossed between the female parent *Vitis rolundifolia* Michx. cultivars 'Supreme' (U.S. Plant Pat. No. 7,267) and the male parent 'Black Beauty' (U.S. Plant Pat. No. 7,592) in 1998. The seedling was selected from a progeny of 187, and testing of the agronomic characteristics began in 2001 in Tallahassee, Fla. The new cultivar was asexually reproduced from cuttings taken from the original seedling and the new cultivar has been tested under the experimental designation O26-1-2. The unique features of the new cultivar have been retained.

Methods of Asexual Reproduction

'Florida Onyx' was asexually reproduced in Tallahassee, Fla., utilizing standard mist propagation techniques. Soft wood cuttings from the original 'Florida Onyx' vine were taken from June through August, the base of the two-node softwood cuttings were first dip-touched briefly with Hormodin-3 root inducing substance (OHP, Inc., PO Box 230, Mainland, Pa.), placed in a 50% sand and 50% peat moss medium, and kept in mist screen house. They were misted for 30 seconds in 10-minute intervals for a period of about 10 hours during the day. After rooting for five or more weeks, the cuttings were transferred into 0.5 gallon pots with potting soil and moved out of the mist bed to a shaded nursery grounds for further developing. Other methods of asexual reproduction are possible. One alternative method comprises layering during later summer through mid-fall, wherein the current season's growth is placed into a trench 20 cm deep at the base of the mother plant, still attached to the mother vine, and covered with soil. Rooting cuttings from the material in the trench can then be separated from the mother plant during the following dormant season, laying may be 100% rooting proof.

Plant Characteristics

The following plant characteristics are relevant for plants that are five years old. Muscadine vines grown from seed will normally take three years to bloom and set fruits. The vine reaches peak production in four to five years. Commercially grown vines are produced by asexual/clonal propagation, from rooted cuttings of the annual growing soft shoots. They can bloom and set fruits in the second year after planting and will reach full fruit production in three to four years.

Vine

The vines of 'Florida Onyx' grow moderately, i.e., the growth of lateral canes on mature vines is at least 1.2 to 2.4 m per growing season. The vines typically fill a 3.6 m single-wire trellis in the second growing season in Florida. The typical five-year-old vine in fruit set of 'Florida Onyx' cultivar have tight, compact, and non-shedding bark with vertical striation and pits and brownish gray color (RHS 200B). The trunk caliper measurement at 30 cm above the soil line averages 3.5 cm.

Shoots

The young 'Florida Onyx' shoot tip is light olive yellow green (RHS 152A), and mature shoots are grayish reddish orange colored (RHS 177D) with average 3.9 cm internodes and 5.1 mm in diameter. Shoots grow erectly to semi-erectly. New shoots from dormant buds typically produce inflorescences at the 3rd and 4th nodes. Inflorescences are compound panicles composed of 10 to 20 flower clusters, each containing 5 to 15 individual female flowers. Tendrils are unbranched, averaged 15 cm in length and 1.8 mm in diameter, and the pith discontinuous along the nodes.

Buds

The development of shoots in the spring results from the emergence of compound buds on the spurs. Each bud arises as an axillary bud meristem in each leaf axil of the shoot in the previous growing season. Potential fruiting clusters, also called inflorescences, are initiated within developing axillary buds the season prior to bloom. The inflorescences may be up to 10 cm long at bloom. The inflorescence is a panicle consisting of flowers arranged within variously branched dichasia. Thus, the main axis is terminated by a flower, as are each of the lateral branches. The flowers start to bloom in late mid-May and are at full bloom in later May to early June.

Foliage

'Florida Onyx' has 8 cm mid-sized, round, unlobed leaves with 20-30 dentate margins and an acuminate point. Leaves average 7.7 cm in length and 7.8 cm in width. The leaves are nearly circular with broadly toothed margins, and glabrous on both upper and lower surfaces. The venation pattern is netted, or reticulate with a greyish reddish orange color (RHS 177D). The mature upper leaf surface is dark green (RHS 136A) and somewhat shiny, while the lower leaf surfaces are moderate yellowish green (RHS 138A) and are not as dark and less bright compared to the upper surface. The leaves become subglabrous at maturity and are deciduous. The petiole is greyish reddish orange (RHS 177D) with the length being equal to or slightly shorter than the blade midrib length and the petiole sinus is half opened. The average petiole is 5.1 cm long and 2 mm in diameter.

Flowers

'Florida Onyx' bears pistillate (female) flowers, which require pollinators to set fruits. Flower are small, unopened flowers at blooming are 2.5 mm in diameter and 2 mm in ovary diameters in open flowers. The flowers are indiscrete, and moderate yellow green (RHS 138C), born in racemose panicles opposite leaves at the base of current season's growth.

The non-functional anthers are light yellow in color (RHS 21D), and supported on short and defected filaments at the base of the ovary. The flowers are short-lived, lasting approximately 3 to 5 days. 'Florida Onyx' typically blooms from May 25 through June 10 at Tallahassee, Fla. Successful pollination of 'Florida Onyx' has been accomplished with 'Alachua' 'Black Beauty', 'Trimph'. Any male and perfect flowers in the species can serve as a pollen source. Both wind and insects play an important role in the pollination of the flowers.

There are 5 each of sepals, petals, and stamens in light yellow green (RHS 150D). Ovaries are superior and contain 2 locules each with 2 ovules. Each cluster has about 10-30 flowers. The calyptera, or cap is the corolla, in which the petals are fused at the apex; it abscises at the base of the flower and pops off at anthesis. Calyptera dry or capping is common in most female muscadine grapes while is rare with 'Florida Onyx'.

Fruits

The vines produce large, dark red colored fruits, which ripen evenly in a 1 to 2-week period beginning around August 20 in Tallahassee, Fla. At maturity, the berries are approximately 16.2 grams each with 15.2% soluble solids (SSC). The firm berry flesh texture would be semi-melt with over-ripened fruits. The berries have typical muscadine aromatic flavor, and relative thick but edible skins along with a brilliant greenish yellow color (RHS 151D). The berries are round to slightly elongated with a 2.92 length (L)×2.78 diameter (D) ratio (1.05 L/D ratio), each berry containing 3.3 seeds on average. The fruit is borne in dense clusters of 4-15 grapes (average 8.7 berries per cluster). The berries have conspicuous lenticels giving them a somewhat mottled appearance. The berries separate from the pedicel with a relatively low wet scar, i.e., more than 80% of the berries are torn at the point of detachment from the pedicel. The black-red color of the 'Florida Onyx' fruit falls into the purple-violet to violet groups (RHS 82A and 83A). This fruit color is distinct from the bronze fruit of 'Triumph', and the black to deep red color of 'Supreme'. A comparison of the important fruit characteristics (size, soluble solids, berry cluster) and overall yield are presented in Table 1 and Table 2, these observations have been made annually over a three year period, and the traits have been retained.

Disease/Pest Resistance or Susceptibility

Like most of the muscadine grapes, 'Florida Onyx' exhibit greater disease tolerance than other American native and European origin grapes. It is highly disease tolerant and practically immune to phylloxera, nematodes, and Pierce's disease (PD) with very low fruit rot and relatively low wet scar. No severe fungal diseases have been observed except slight leaf spot late in the season.

Ripening rot which including but not limited to Bitter Rot (pathogen *Greeneria uvicola*), Ripe Rot (pathogen *Colletotrichum* sp.), and Macrophoma Rot (pathogen *Botryosphaeria dothidea*), is 5.2% on average, similar to that of 'Ison', while much lower than that of 'Supreme' (Table 1).

TABLE 1

Horticultural characteristics of 'Florida Onyx' and leading table muscadine cultivars in Tallahassee, FL

| | flower type | vigor | node length (cm) | node circle (cm) | leaf size (L × W) (cm) | pruning weight (kg) |
|---|---|---|---|---|---|---|
| Fry | female | m-w | 3.9 | 1.5 | 7.8 × 7.8 | 3.2 |
| Black Beauty | perfect | M | 4.2 | 1.7 | 8.3 × 8.3 | 5.1 |
| Majesty | female | M | 4.3 | 1.8 | 8.3 × 8.5 | 3.9 |
| Supreme | female | m-w | 3.8 | 1.5 | — | 2.5 |
| Florida Onyx | female | M | 4.3 | 1.9 | 7.7 × 7.8 | 4.1 |

| | PD (0-5) | cluster/ spur | cluster/ shoot | fruit/ cluster | yield (kg/ vine) | dry scar (%) | harvest fruit rot (%) |
|---|---|---|---|---|---|---|---|
| Fry | 0 | 2.5 | 1.4 | 7.0 | 19.4 | 84.5 | 18.9 |
| Black Beauty | 0 | 2.8 | 1.6 | 9.7 | 25.5 | 86.0 | 5.2 |
| Majesty | 0 | 2.2 | 1.3 | 6.2 | 21.6 | 84.6 | 6.4 |
| Supreme | 0 | 2.6 | 1.5 | 7.1 | 20.1 | 83.1 | 5.6 |
| Florida Onyx | 0 | 2.5 | 1.4 | 8.7 | 22.6 | 88.9 | 5.2 |

TABLE 2

Fruit characteristics of 'Florida Onyx' and leading table muscadine cultivars in Tallahassee, FL

| | Color | Shape (L/W) | Size (g) | SSC (%) | TA (%) | pH | Seeds/ fruit |
|---|---|---|---|---|---|---|---|
| Fry | Bronze | 0.99 | 10.3 | 16.2 | 0.40 | 3.36 | 3.5 |
| Black Beauty | black red | 1.10 | 9.7 | 15.0 | 0.41 | 3.27 | 3.8 |
| Majesty | black red | 0.95 | 16.5 | 15.4 | 0.37 | 3.58 | 2.9 |
| Supreme | black red | 1.04 | 12.8 | 14.0 | 0.40 | 3.24 | 3.6 |
| Florida Onyx | black red | 1.05 | 16.2 | 15.2 | 0.38 | 3.57 | 3.3 |

| | Fruit rot rate (%) during 40° F. storage[1] | | | |
|---|---|---|---|---|
| | Day 7 | Day 13 | Day 21 | Day 28 |
| Fry | 0 | 4 | 33 | 87 |
| Black Beauty | 0 | 2 | 12 | 46 |
| Majesty | 0 | 0 | 17 | 47 |
| Supreme | — | — | — | — |
| Florida Onyx | 0 | 0 | 6 | 34 |

[1]accumulated rot rate, evaluated in 2014

Annual Growth Cycle of Grapevine

'Florida Onyx' buds break at the end of March to early April, bloom later May to early June, fruits set in early to mid-June, veraison starts in early July, fruits ripen evenly at mid to late August until the beginning of September, and leave fall in December in Tallahassee, Fla.

What is claimed is:

1. A new and distinct variety of muscadine grape plant named 'Florida Onyx', substantially as herein described and illustrated.

* * * * *

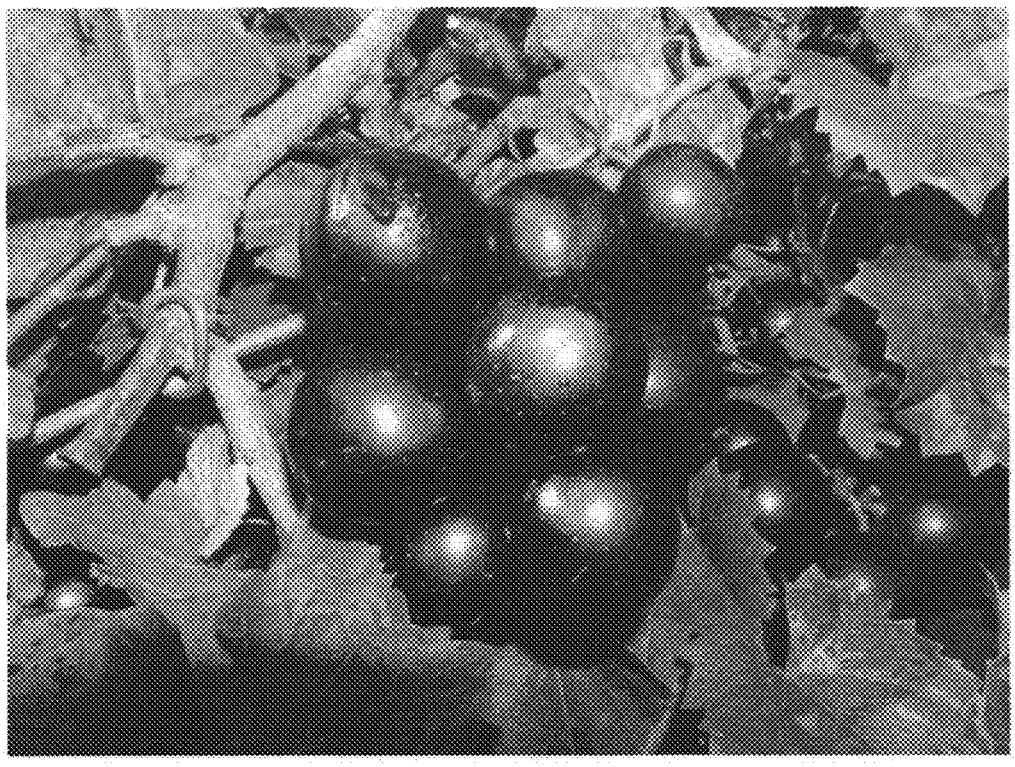
FIG 1. Onyx: mature cluster

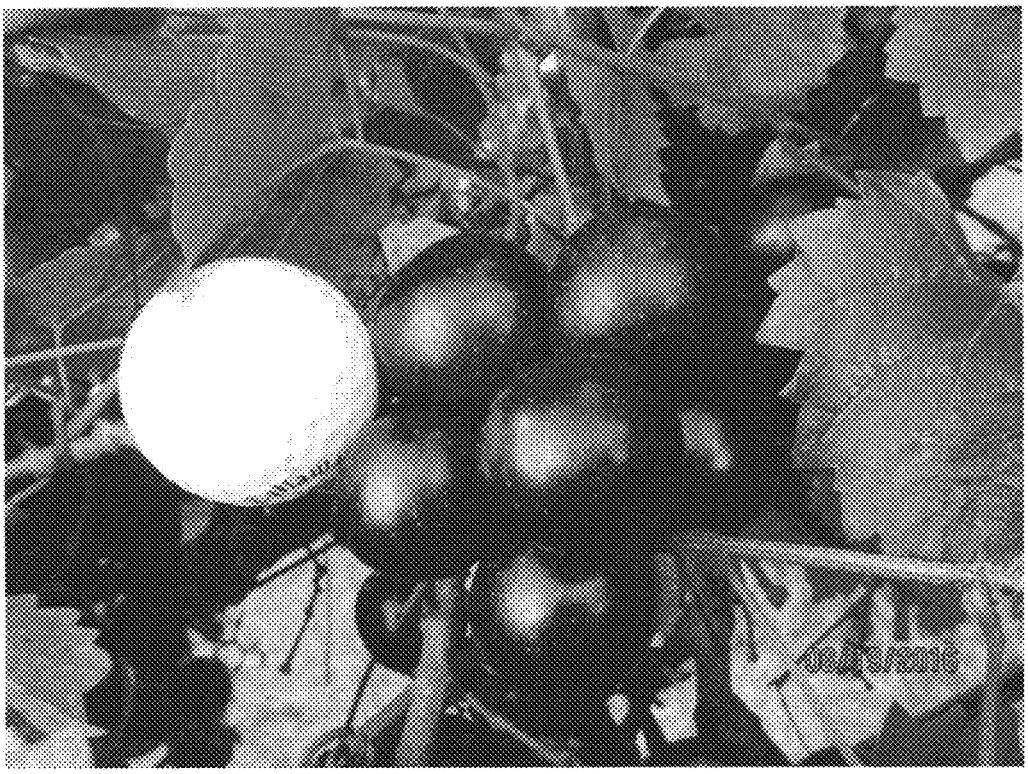
FIG 2. Onyx: mature berry size in comparison to a golf ball